(12) United States Patent
Laubsch et al.

(10) Patent No.: US 12,703,847 B1
(45) **Date of Patent: *Aug. 11, 2026**

(54) PROCESS FOR PRODUCING A BIO-INACTVE AND SHELF STABLE BIOMASS MATTER DERIVED FROM BIOACTIVE BIOMASS FEEDSTOCK

(71) Applicant: Green Recovery Technologies LLC, New Castle, DE (US)

(72) Inventors: Kenneth L. Laubsch, Mullica Hill, NJ (US); Richard R. Masi, Middletown, DE (US); Ashley A. Cephas, Clayton, DE (US)

(73) Assignee: Green Recovery Technologies LLC, New Castle, DE (US)

( * ) Notice: Subject to any disclaimer, the term of this patent is extended or adjusted under 35 U.S.C. 154(b) by 394 days.

This patent is subject to a terminal disclaimer.

(21) Appl. No.: 18/446,124

(22) Filed: Aug. 8, 2023

Related U.S. Application Data

(63) Continuation-in-part of application No. 15/931,865, filed on May 14, 2020, now Pat. No. 11,758,927.

(51) Int. Cl.
*C12M 1/00* (2006.01)
*C12M 1/02* (2006.01)

(52) U.S. Cl.
CPC ............ *C12M 47/14* (2013.01); *C12M 29/24* (2013.01); *C12M 41/18* (2013.01)

(58) Field of Classification Search
CPC ............................... A23K 30/20; C12M 47/14
See application file for complete search history.

(56) References Cited

U.S. PATENT DOCUMENTS

2016/0183565 A1 6/2016 Rudinger et al.

FOREIGN PATENT DOCUMENTS

WO WO-2006084943 A1 * 8/2006 ............... B09B 3/35

OTHER PUBLICATIONS

Downs, "Suitability of a dehydrated poultry mortality-soybean meal product for use in broiler chicken diets", J. Appl. Poult. Res., 2002, 12, 222-228 (Year: 2003).

* cited by examiner

*Primary Examiner* — Changqing Li
(74) *Attorney, Agent, or Firm* — Devlin Law Firm LLC

(57) ABSTRACT

A process for producing a bio-inactive and shelf stable biomass matter derived from bioactive biomass feedstock includes processes that can be performed in an effective way with equipment that does not require large expenditures. The biomass feedstock may be dewatered and then stabilized to prevent degradation. The stabilized biomass may then be back blended with a dried back blending biomass having a water concentration of less than 10% and a particle size that produces back blended biomass that can be effectively processed by controlled agitation drying wherein the thickness is maintained at less than 100 mm while an airflow is formed over the back blended biomass and shear mechanical energy is imparted. The entire process may be performed in less than 12 hours to produce a shelf-stable dried biomass.

21 Claims, 2 Drawing Sheets

PROCESS FOR PRODUCING A BIO-INACTVE AND SHELF STABLE BIOMASS MATTER DERIVED FROM BIOACTIVE BIOMASS FEEDSTOCK

CROSS REFERENCE TO RELATED APPLICATIONS

This application is a continuation in part of U.S. patent application Ser. No. 15/931,865, filed on May 14, 2020 and currently pending; the entirety of which is hereby incorporate by reference herein.

BACKGROUND OF THE INVENTION

Field of the Invention

The invention relates a process for producing a bio-inactive and shelf stable biomass matter derived from bioactive biomass feedstock.

Background

Bioactive biomass feedstocks are routinely converted to biomass matter that is bio-inactive and the process for producing this valuable commodity requires large capital expenditures, large operating costs and typically takes a long period of time. The state of the art generally relies on using thermal energy at high temperatures, above 100° C. (212° F.) typically to dry the biomass and make it inactive. The thermal energy can come from a tunnel dryer, spray dryer, paddle dryer or similar device. Conventional drying of biomass feedstocks is performed at temperature as high as 343° C. (650° F.). This high heat thermally degrades nutrients and products, degrades protein to make them less digestible, and converts fats to free fatty acids, which promotes rancidity.

SUMMARY OF THE INVENTION

The invention is directed to a process for producing a bio-inactive and shelf stable biomass matter derived from bioactive biomass feedstock. A bio-inactive biomass matter is produced in an efficient and effective way with equipment that does not require large capital expenditures and significantly lower operating costs.

In an exemplary embodiment, a bioactive biomass feedstock is a biomass comprising protein, fat and water and is derived from a meat processing facility. The biomass feedstock may include animal matter and proteins from various parts of an animal and may also include carbohydrates. The biomass feedstock may include animal matter from fowl, poultry, chickens, cows, pigs, fish, lamb and the like. In an exemplary embodiment, the biomass feedstock is derived from vegetable matter, comprising protein, fat, water, carbohydrates, fiber, minerals, and pigments. A biomass feedstock may include an original concentration of protein, fat and water. The original protein concentration may be from about 2.5% to 66% by weight of the biomass feedstock. The original fat concentration, which may include fats, triglycerides, free fatty acids, oils, greases and related lipid materials, may be from about 2.5% to 66% by weight of the biomass feedstock. The original water concentration may be from about 50% and 85%, or from about 50% to 98% by weight of the bioactive biomass feedstock. It may be preferred that the original protein concentration is at least 10%, the original fat concentration is less than about 10% and the original water concentration is less than 90%.

The bioactive biomass feedstock may be initially bulk dewatered to reduce the water concentration to no more than 90% and preferably to no more than about 75% and more preferably no more than 50% and even more preferably no more than 20% of the original water concentration of the bioactive biomass feedstock. The initial bulk dewatering process step may be performed by pressing with a belt or screw press, by centrifugation utilizing a decanting or tricanting centrifuge, by the addition of dewatering compounds to the bioactive biomass feedstock, by electrochemical means including electrocoagulation, by thermal means including exposure to low temperature below about 50° C. (122° F.) for long durations of about an hour or more, or two or more hours, six or more hours, ten or more hours, or high temperature above about 50° C. (122° F.) for short duration of less than about 12 hours, such as ten hours or less, two hours or less, 30 minutes or less, 15 minutes or less, 5 minutes or less, or 1 minute or less, or even about 30 seconds or less, or even 10 seconds or less. If thermal means are used, this can include direct heating, indirect heating, heated air or inert gas impingement, such as by use of an inert gas such as nitrogen. In an exemplary embodiment, during controlled drying the airflow consists substantially of nitrogen, having at least a 90% concentration of nitrogen. When the temperature of the airflow is high and/or at a higher airflow rate or volume the duration may be lower. The water in the bioactive biomass feedstock may exist as both free water and bound water within the system. This free water can be advantageously mechanically removed before thermal or thermo-mechanical removal through screw dewatering augmented with chemical and electrochemical means. The water may be removed with low capital cost equipment to produce a dewatered bioactive biomass feedstock and the initial dewatering may be done at low temperatures, below about 50° C. (122° F.).

The initial bulk dewatering process step may be enhanced through the addition of dewatering compounds to the bioactive biomass feedstock including but not limited to general category flocculants (synthetic or natural flocculants). The addition of dewatering compounds such as flocculants coupled with agitation, aeration, mixing and/or shearing process may quickly and effectively dewater the bioactive biomass feedstock. Flocculants encourage solid particles to adhere to one another in clumps, or flocs, through charge bridging, electrostatic patching, and magnetic neutralization. The solids coalesce into larger bodies where free water can be forced out and the remaining lower moisture solids collected for further processing. Examples of coagulants include, but are not limited to, metal salts (sulfides and chlorides of aluminum and iron), naturally occurring materials or compounds including chitosan, alum, synthetic compounds such as polymeric compounds including Polydiallyldimethylammonium chloride (i.e. DADMAC), polyamines including EPI-DMA of various molecular weights.

Another dewatering compound that may be used are coagulants which may be aluminum or iron-based chemicals that change the magnetic charge of particles in the water, causing them to attract instead of repel each other. Again, the solids coalesce into larger bodies enabling free water to be forced out and the remaining lower moisture solids collected for further processing. An exemplary surfactant is laurel sulfate.

Another dewatering compound that may be used are surfactants that promote particle adhesion. A surfactant may be used with other dewatering compounds to increase the effectiveness of dewatering.

Another dewatering compound is a pH adjuster that alters the pH of the bioactive biomass feedstock which include, but are not limited to, bases including potassium hydroxide, sodium hydroxide, and acids including sulfuric, hydrochloric, nitric, acetic and citric. The bulk dewatered biomass may then be stabilized to minimize free fatty acid creation, oxidation of the fats, oils and greases and to produce a stabilized biomass. The stabilized biomass may include a stabilized fat that prevents oxidations and has the stabilized biomass may have a free fatty acid concentration of less than 50% by weight of the total fat content in the stabilized biomass. The biomass may be stabilized by adding a stabilizer, such as an antioxidant, or by subjecting the dewatered biomass to ultraviolet light or radiation, or by exposure to high isostatic pressure and rapid depressurization. An antioxidant may be sprayed onto the dewatered biomass to ensure effective distribution of the antioxidant. The antioxidant stabilizer may be added in a dosing concentration of 2 to 20,000 parts per million. An exemplary stabilized biomass thus treated by any, or some or all of the aforementioned techniques may have less than 40% free fatty acids and preferably less than 20% by weight of the total fat content, as measured directly via common analytical techniques such as wet chemical extraction, Fourier-transform infrared spectroscopy (FTIR), gas chromatography or liquid chromatography or measured indirectly via peroxide value or similar fat rancidity measurement.

The stabilized biomass may then be mixed by back blending with a back blending biomass or supplemented external protein source or extracted defatted protein which has a water concentration of no more than 50% and preferably no more than 10% and even more preferably no more than 5%, and an average particle size of between 10 and 20,000 microns, and preferably between 400 and 10,000 microns, with a most preferred size of between about 800 and 5,000 microns, or about 2,500 microns. Particle sizing may be observed and measured utilizing a commercial instrument utilizing any of the following techniques: Coulter principle, laser diffraction, light scattering or polarized intensity differential scattering and the Brumaire, Emmett and Teller (BET) method, with the Coulter principle being preferred. Particle size, including average particle size, may be determined using a particle size analyzer, available from Beckman Coulter, Indianapolis, IN. The lower the water concentration of the back blending biomass, the faster the initial reduction in the mixture water concentration and the quicker the mixture may be subsequently dried. The particle size of the back blending biomass is important, as too small of a particle produces a viscous sludge that is not effectively processable in subsequent process steps or clogs filters, and too large of a particle size does not produce a homogeneous mixture. A mill such as a shear mill, pug mill or colloidal mill can be used to adequately size the particles entering the drying operation. The back blending biomass may be derived from the same biomass feedstock or may comprise different components or ratios of components than the biomass feedstock or stabilized biomass. The mixing ratio of the back blending biomass to the stabilized biomass may be from about 0.1:1 to 5:1 to reduce water concentration to be 75% or less, or preferably at least 50% or less of said original water concentration of the bioactive biomass feedstock and to promote granularization of back blended biomass. The back blended biomass may have a resulting water concentration of about 10% or more, about 30% or more, about 50% or more, or even about 60% or less, or from about 10% to 60% and any other range between and including the values provided. A more preferred mixing ratio may be from between 0.3:1 to 3:1. Back blending may be performed with any suitable mixing equipment including a mixer, such as a drum mixer, or blender, such as a ribbon blender.

The stabilized biomass may be spread out on a drying surface, such as any planar ground surface, or platform, such as a concrete floor or similar surface, a metal cylinder or within a trough and back blending biomass may be added using a tractor with a mixing head attachment or similar device to effectively promote mixing and granularization. The stabilized biomass may be mixed with the back blending biomass prior to spreading the back blended biomass onto a drying surface. The drying surface may also be heated. The spread thicknesses, or thickness of a layer of biomass on a planar surface will depend on the water concentration and the ratio of the back blending biomass added. For example, the spread thickness may be from about 5 mm to 15.25 cm, with a thickness of at least 20 mm preferred when applied on a surface, such as a non-planar surface. Drying may be performed within an enclosure, such as within an enclosure with airflow openings, such as a tube or a trough, as in a machine with constrained volume mechanical agitation and exposure to drying elements within the machine such as paddles or blades. The surfaces within the enclosure may be planar or non-planar, such as being corrugated or pleated to increase the surface area for quicker drying times. The machine may use mixing implements, such as paddles or blades to mix or macerate the stabilized biomass, in total or a portion of the stabilized biomass. Furthermore, the machine may produce an airflow through the machine and through or over the stabilized biomass. A portion of the stabilized biomass may be dried by the drying machine before being exchanged by a new portion of stabilized biomass for drying.

The granular back blended biomass is then subjected to controlled agitation drying wherein shear mechanical energy is imparted to the back blended biomass under controlled environmental conditions. The controlled agitation may be performed in a covered building, or enclosed building having an enclosed space for the process or enclosure of suitable surface area to house the processing operation and to enable an effective spread thickness for the biomass. The enclosed space of the enclosure may be environmentally controlled to provide an effective environment for rapid drying of the back blended biomass. The enclosed space may be a machine such as a commercially available mixing device modified to include the necessary elements of shear, introduction of drying jets, laminar and/or turbulent heated air streams and blades or paddles designed to expose the biomass to an ideal ratio of drying air and designed to evacuate the drying air and allow for introduction of more drying air with an efficient plug flow or turbulent flow system for saturated air flow removal. The back blended biomass may be spread to a particular thickness, as described herein, on surface, such as a planar surface. The surface may be heated from above and/or below utilizing radiant, conductive and convective heat sources. An exemplary heating element is configured in the surface and may include a resistive heating element or a conduit for receiving a flow of heated fluid through the conduit, which heats the surface through radiant, convective and conductive means. For example, a heating element may be configured in a floor, such as a concrete floor and the back blended biomass may be heated by conduction. An exemplary heating element may be configured above the surface and may include a resistive heating element or similar device. In an exemplary embodiment, a heating element is configured below the back blended biomass, such as in the floor or processing surface and also above the biomass such as a radiant heating element, such as an infrared lamp. Also, note that a heated flow of air may be produced to flow over the back blended biomass during controlled agitation drying to assist in convective heating. A preferred heater utilizes scavenged heat from an auxiliary heat source such as machine vessel heat transfer fluid through a heat exchanger, or from a blower having heat of compression that is recovered or a motive force that is employed for the direct drying air source or motive force for removal of saturated atmosphere above the biomass. Also, discharge from a blower may be partially reintroduced into the blower or air compressor to increase the inlet temperature of the machine to increase the temperature of the airflow from the blower or compressor and increase the moisture holding capacity of the drying air steam applied to or maintained over the biomass.

An airflow may be forced over, around or through the back blended biomass during the controlled drying and agitation may also be imparted to the biomass during the controlled drying step. The airflow during the controlled agitation drying process may be about 15.2 m/min (50 fpm) to about 305 m/min (1,000 fpm) and preferably at least 30.5 m/min (100 fpm) or at least 122 m/min (400 fpm). The relative humidity level may be maintained substantially between 5% and 100%, or substantially between 5% and 65% over the process, during at least 80% of the controlled agitation time. When even hotter air streams are directed to have intimate contact with the biomass, the relative humidity of the exiting airstream may be saturated or even supersaturated. Humidity levels may spike initially or while agitating, however. The temperature of the back blended biomass may be maintained between about 10° C. (50° F.) and 54.4° C. (130° F.) or between about 10° C. (50° F.) and 71.1° C. (160° F.) over at least 50% of the controlled agitation drying time to produce a bio-inactive and shelf stable biomass matter having a final water concentration of no more than 12% by weight, or no more than 10% by weight. The temperature of the airflow during the controlled drying step may be an ambient temperature or may be maintained at a temperature of less than 50° C. (122° F.) or less than 45° C. or above about 25° C. for a substantial portion of the controlled agitation time. The airflow may be a high temperature such as about 93.3° C. (200° F.) or more, or even up to about 149° C. (300° F.), for a short duration of about 2 hours or less and preferably less than about 1 hour to maintain a low temperature of the biomass during the controlled drying. Agitation of the biomass during higher temperature airflow may prevent the biomass from becoming too hot. Agitation of the biomass may enable drying at higher temperatures at a quicker rate without denaturing the proteins in the biomass.

The biomass may be subjected to the controlled agitation until the mixture reaches its equilibrium moisture content (EMC), which indicates a final water concentration of no more than 12%, or no more than 10% and preferably no more than 8%. This controlled agitation process may effectively dewater the back blended mixture to produce a dried biomass and to suspend biologic activity. The total time for the entire process, or out time, may be kept to less than 12 hours which prevents biological activity from consuming the feedstock due to aerobic anaerobic degradation. The controlled agitation drying may reduce the water concentration to no more than 10% in less than about 8 hours, or preferably in less than about 6 hours and even more preferably in less than about 4 hours. This short drying time is important to keep the overall out time, or total time for the process to less than 12 hours, and preferably less than 8 or even 6 hours.

The controlled agitation drying may be performed utilizing low capital cost equipment including, but not limited to, a high shear aerator or a rotary tiller. Ideally, the aerator or tiller is attached via a hydraulic power take off to a powered vehicle such as an agricultural tractor or similar device. Agitation may be conducted in tandem with a drag behind aerator or scraper so that the surface of the biomass is continually scored to release residual moisture into the atmosphere. Alternatively, acoustic pulses may be introduced into the biomass to promote initial and accelerated drying. The spread thickness of the back blended biomass mixture may be maintained to no more than about 100 mm, or no more than about 50 mm and preferably no more than about 35 mm, to promote drying during the controlled agitation drying process. The agitation in the embodiment of a trapped volume mixing and drying device is most effectively introduced with an electric motor, or hydraulic motor, or other rotary and linear actuation devices, to effect agitation, impart shear force, and/or expose the biomass to an agitation to increase surface area exposure.

The dried biomass may further be sterilized using a sterilant such as peracetic acid, or by exposure to ultraviolet light or radiation or by exposure to high burst, short duration pulsed acoustic energy, or by high temperature, short duration pasteurization or extrusion. Shelf stable as defined herein, means that the biomass is viable for further processing and bio-inactive, whereby it does not self-degrade for a minimum of 6 months when properly stored in sealed totes, supersacks or containers with typical shelf life of two or up to three years.

The dried biomass has a final concentration of protein of about 40%, fat of about 45%, water of about 8% and ash of about 7%. The dried biomass has a final concentration of protein of about 30% or more, a fat concentration of about 65% or less, and a water concentration of about 10% or less. Ash is solid material or particles in the mixture that are not recognized as protein, fat or water and may be bone particles and other materials. The protein concentration in the dried biomass may range from about 25% to 60%, and preferred as high as possible. The fat concentration in the dried biomass may range from about 25% to 60% with lowest concentration being preferred. Moisture or water in the dried biomass may range from about 6% to about 14% with lowest being preferred. Ash in the dried biomass may range be less than about 14%, or preferably less than about 8% or less than about 6%; the smallest amount is desirable.

Biomass, as used herein, is defined as any organically-derived matter, either in waste or whole product, plant or meat based, that can be used as a food and/or energy source. The biomass feedstock may be flocculated or non-flocculated in nature and may be a commingled waste streams as well as non-waste streams.

Bioactive, as used herein, is defined as an organic or inorganic material containing biological agents such as bacteria, viruses, molds, mildews, and the like, that have the effect of degrading and/or consuming the material, causing it to rot, degrade thereby losing value Bio-inactive, as used herein, is defined as an organic or inorganic material where biological agent activity has been suspended based on thermal, chemical or related treatments. A bio-inactive material may not be sterile, but the biological agents are not able to grow and propagate due to low moisture, low oxygen, high chemical, high pH characteristics. There are numerous test kits available commercially that use biological, biochemical, molecular, or chemical methods for the detection, identification or enumeration of microorganism activity in a material.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
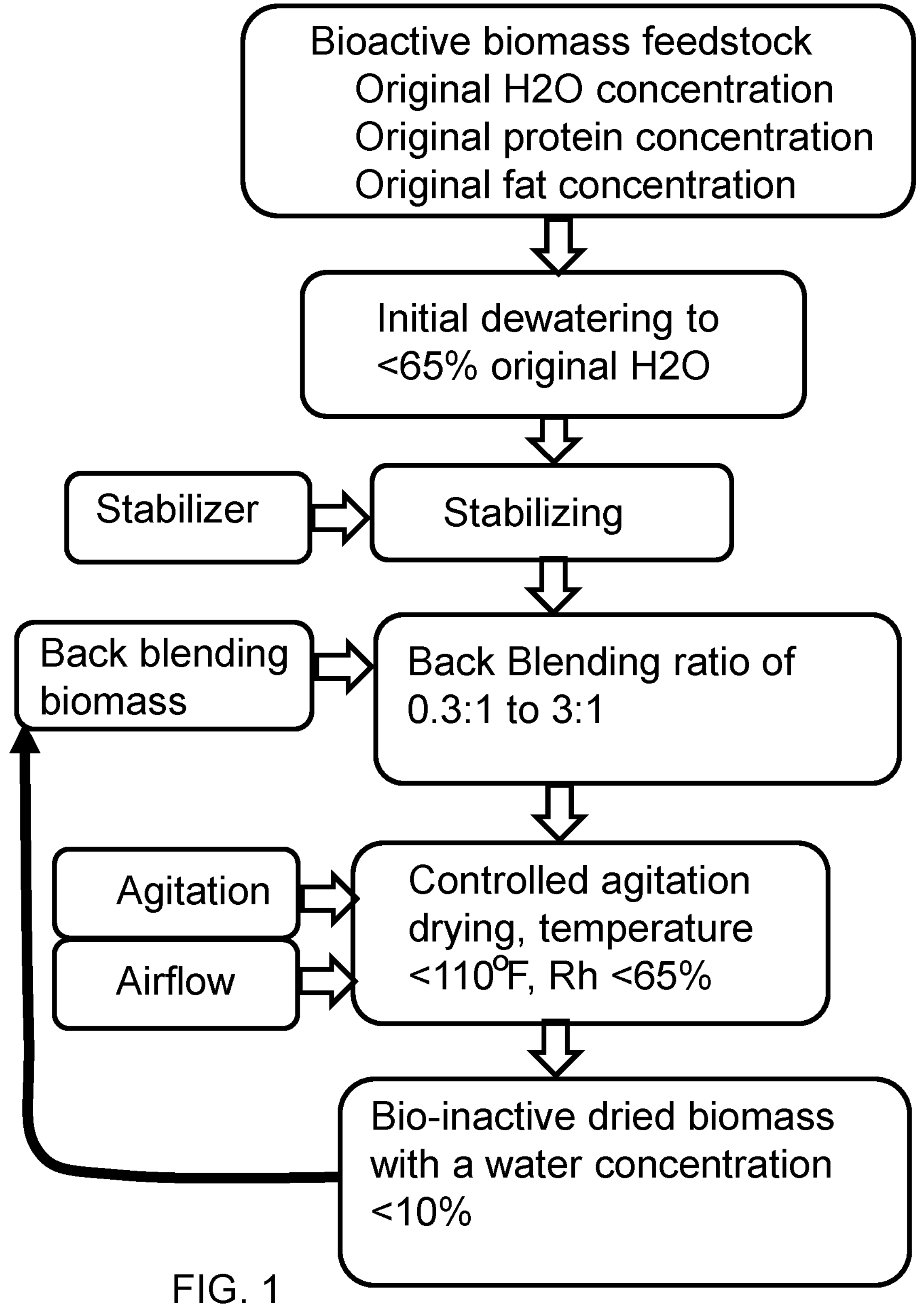
FIG. 1 shows an exemplary process for producing a bio-inactive and shelf stable biomass matter derived from bioactive biomass feedstock.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, a bio-inactive dried biomass is produced from a bioactive biomass feedstock in a short amount of out time to prevent biologic activity. The bioactive biomass feedstock is dewatered to a dewatered water concentration that is no more than 65% that of the original free water concentration. A stabilizer is then provided and added to the dewatered biomass. A back blending biomass is then back blended with the stabilized biomass in a ratio of 0.3:1 to 3:1 of back blended biomass to stabilized biomass. The back blending biomass may be the product of this process from a former batch and may be derived from the same biomass feedstock, as indicated by the bold arrow from the final bio-inactive dried biomass to the back blended biomass input. The back blended biomass mixture is then agitated by imparting shear mechanical energy in an environmentally controlled condition, including imparting an airflow over the back blended biomass mixture while maintaining a relative humidity level of between 5% and 100%, or between 5% and 65%, and maintaining a temperature of less than 43.4° C. (110° F.) over a substantial portion of the controlled agitation drying, or at least 50% of the controlled agitation drying time, and preferably at least 75% of the controlled agitation drying time, and even more preferably at least 90% of the controlled agitation drying time. This entire process is performed in an out time of no more than 12 hours which arrest bioactivity to produce a dried biomass that is shelf stable for an extended period of time.

Figure 2:
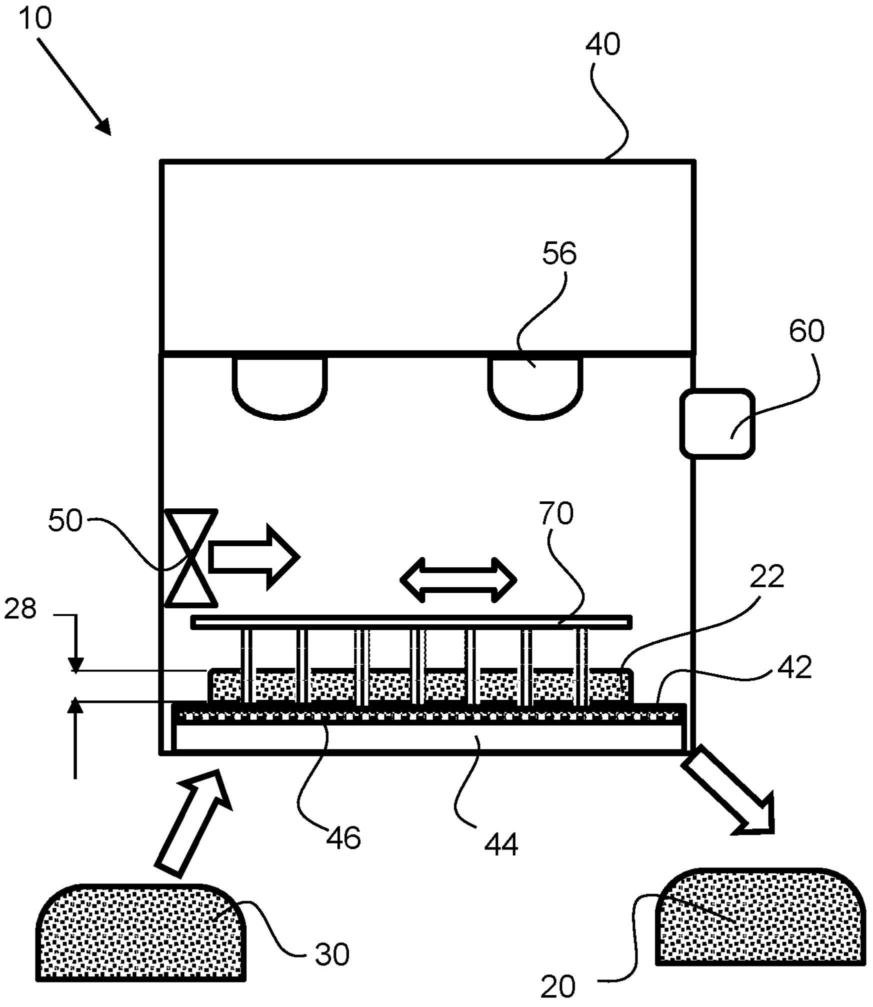
FIG. 2 shows a diagram of an exemplary bio-inactive and shelf stable biomass matter processing system.

FIG. 2 shows a diagram of a bio-inactive and shelf stable biomass matter processing system 10, wherein the bio-inactive and shelf stable biomass matter 20 is derived from a bioactive biomass feedstock 30. As shown a back blended biomass 22 is configured on a planar surface 42, such as a radiant floor 44 that is heated, within an enclosure 40, such as a building having an enclosed space that can be environmentally controlled. The radiant floor may have a heating element 46, such as conduits for receiving a flow of heated fluid configured therein or thereon. An air moving device 50, such as a fan may produce a flow of air over the spread back blended biomass 22 to increase the rate of drying. A heating element 56 may be configured to increase the temperature of the enclosure or the environmental temperature or impart radiant energy, such as infrared energy onto the surface of the biomass material. A humidity control device 60 may be configured to reduce the humidity level within the enclosure. A mechanical energy device 70 is configured to impart mechanical mixing energy into the back blended biomass to mix the granulated matter to expose higher moisture content granules to the exposed outside surface of the spread layer and allow trapped water vapor to escape from the biomass into the airflow thereover. The spread thickness 28, may be maintained at an effectively low thickness to enable the back blended biomass to be dried to a desired level within a desired out time.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A process for producing a bio-inactive and shelf stable biomass matter derived from bioactive biomass feedstock comprised of the following:

a) providing said bioactive biomass feedstock comprising:

i) an original protein concentration of between 2.5% and 66% by weight of the bioactive biomass feedstock;

ii) an original fat concentration of between 2.5% and 66% by weight of the bioactive biomass feedstock; and iii) an original water concentration of between 20% and 90% by weight of the bioactive biomass feedstock;

b) stabilizing the bioactive biomass feedstock by adding an antioxidant at a dosing concentration of 2.0 to 20,000 parts per million by weight of the bioactive biomass feedstock to said bioactive biomass feedstock to produce a stabilized biomass wherein the fat is stabilized to prevent oxidation and to minimize free fatty acid creation to less than 50% by weight of the original fat concentration of the bioactive biomass feedstock;

c) providing a blending dried biomass, having a particle size between 10 and 20,000 microns;

d) back blending the stabilized biomass by mixing with the back-blending dried biomass at a back blending ratio by weight of said blending dried biomass to said stabilized biomass to produce a back blended biomass having a water concentration by weight that is 75% or less than said original water concentration of the bioactive biomass feedstock so that the biological activity does not consume the bioactive biomass feedstock via aerobic degradation processes and e) controlled drying of the back blended biomass by producing controlled drying environment conditions including producing an airflow over the back blended biomass, maintaining a humidity level of between 5% and 100%, and maintaining a temperature of the back blended biomass between 10° C. (50° F.) and 71.1° C. (160° F.) over at least 50% of the drying time to produce said bio-inactive and shelf stable biomass matter having a final water concentration of no more than 10% by weight;

wherein a total duration time for processing said bioactive biomass feedstock in step a) to said bio-inactive and shelf stable biomass matter in step e) is controlled to less than 12 hours so that the bioactive biomass feedstock is not consumed by aerobic degradation processes.

2. The process of claim 1, wherein the controlled drying of the back blended biomass further includes agitation of the back blended biomass by imparting shear mechanical energy while producing said controlled drying environment conditions.

3. The process of claim 2, further comprising providing a shear aerator and wherein the shear mechanical energy is imparted to the back blended biomass using said shear aerator.

4. The process of claim 1, further comprising bulk dewatering the bioactive biomass feedstock to reduce the original water concentration of the bioactive biomass feedstock to no more than 75% by weight of the original water concentration of the bioactive biomass feedstock.

5. The process of claim 4, wherein bulk dewatering includes decanting the bioactive biomass feedstock to remove water from the bioactive biomass feedstock.

6. The process of claim 4, wherein bulk dewatering includes centrifuging the bioactive biomass feedstock to remove water from the bioactive biomass feedstock.

7. The process of claim 4, wherein bulk dewatering includes pressing the bioactive biomass feedstock to remove water from the bioactive biomass feedstock.

8. The process of claim 4, wherein bulk dewatering includes adding dewatering compounds to the bioactive biomass feedstock to remove water from the bioactive biomass feedstock.

9. The process of claim 4, wherein bulk dewatering includes exposing the bioactive biomass feedstock to electro-coagulation to remove water from the bioactive biomass feedstock.

10. The process of claim 1, wherein the blending dried biomass has an average particle size of between 100 and 10,000 microns.

11. The process of claim 1, wherein the controlled drying of the back blended biomass includes spreading the back blended biomass on a surface forming a spread thickness of the back blended biomass of no more than 15 cm.

12. The process of claim 11, wherein the surface is configured within a non-planar enclosure and wherein the controlled drying environment conditions are controlled within said enclosure.

13. The process of claim 11, wherein the surface is a radiant surface comprising a heating element to heat said radiant surface.

14. The process of claim 1, wherein the airflow during the controlled drying is maintained between 15.24 m/min (50 fpm) and 305 m/min (1000 fpm).

15. The process of claim 1, wherein the airflow during the controlled drying is maintained between 10° C. and 149° C. (50° F. and 300° F.).

16. The process of claim 1, wherein the airflow during the controlled drying is turbulent airflow.

17. The process of claim 1, wherein the airflow during the controlled drying consists substantially of nitrogen, having at least a 90% concentration of nitrogen by volume.

18. The process of claim 1, wherein the bioactive biomass feedstock comprises an animal-based feedstock stream.

19. The process of claim 1, wherein the bioactive biomass feedstock comprises a plant-based coproduct stream.

20. The process of claim 1, wherein the controlled drying includes particle sizing through acoustic or ultrasonic pulses.

21. The process of claim 1, wherein the controlled drying includes using scavenged heat from the controlled drying.

* * * * *